United States Patent [19]
Hood

[11] Patent Number: 5,372,709
[45] Date of Patent: Dec. 13, 1994

[54] FLUID FLOW CONTROL APPARATUS

[75] Inventor: Robert G. Hood, Paisley, Scotland

[73] Assignee: Bio-Flo Limited, Glasgow, Scotland

[21] Appl. No.: 70,635

[22] Filed: Jun. 1, 1993

Related U.S. Application Data

[63] Continuation of Ser. No. 689,246, Aug. 14, 1991, abandoned.

[30] Foreign Application Priority Data

Dec. 13, 1988 [GB] United Kingdom ............... 8829311

[51] Int. Cl.$^5$ ............... B01D 17/12; B01D 61/32
[52] U.S. Cl. ............... 210/90; 210/137; 210/416.1; 210/929; 251/9; 417/26; 417/474; 422/48; 422/112; 604/4; 604/65
[58] Field of Search ............... 210/90, 97, 102, 134, 210/137, 143, 321.65, 416.1, 646, 929, 96.2, 321.71; 138/43, 45, 46, 119; 251/4, 6, 7, 9; 417/26, 28, 474, 476, 477, 475; 422/100, 101, 103, 105, 112, 45, 48; 604/25, 31, 34, 65, 67, 250, 4-6

[56] References Cited

U.S. PATENT DOCUMENTS

| | | | |
|---|---|---|---|
| 3,386,382 | 6/1968 | Schuette et al. | 251/9 |
| 3,774,762 | 11/1973 | Lichtenstein | 210/929 |
| 3,946,731 | 3/1976 | Lichtenstein | 210/929 |
| 4,229,299 | 10/1980 | Savitz et al. | 417/477 |
| 4,266,559 | 5/1981 | Akhavi | 128/766 |
| 4,266,751 | 5/1981 | Akhavi | 251/6 |
| 4,370,983 | 2/1983 | Lichtenstein | 210/321.65 |
| 4,425,116 | 1/1984 | Bilstad et al. | 604/6 |
| 4,479,760 | 10/1984 | Bilstad et al. | 604/6 |
| 4,479,761 | 10/1984 | Bilstad et al. | 604/6 |
| 4,713,051 | 12/1987 | Steppe et al. | 604/35 |
| 4,838,865 | 6/1989 | Flank et al. | 604/4 |

FOREIGN PATENT DOCUMENTS

A0229504 7/1987 European Pat. Off. .

OTHER PUBLICATIONS

Article by Gousuke Anno and Hideo Hidai "Transmembrane pressure stabiliser for haemodialysis", printed from Biomedical Engineering, Jan. 1976.

Primary Examiner—Joseph W. Drodge
Attorney, Agent, or Firm—Pennie & Edmonds

[57] ABSTRACT

A fluid control apparatus for use in separation and filtration having a removable sterilizable and disposable element which is engagable with a fixed element in the apparatus. When the two elements are engaged, the flow of fluid around a fluid circuit is controlled to optimize separation. The elements contain various conduits and inlet and outlet ports that function to deliver fluid to and from separation and filtration systems such as life support systems.

27 Claims, 5 Drawing Sheets

FLUID FLOW CONTROL APPARATUS

This is a continuation, of application Ser. No. 07/689,246, filed Aug. 14, 1991, now abandoned.

The present invention relates to fluid flow control apparatus and particularly, but not exclusively, to fluid control apparatus for use in separation and filtration systems.

Fluid flow control apparatus for use in separation and filtration systems and similar fluid handling systems such as a life support system should satisfy a number of desirable criteria in addition to being efficient and relatively inexpensive. The constituent parts of the fluid control apparatus should be easily cleaned or sterilised or be disposable as this is important when using biological fluids such as blood. The apparatus should require minimal fluid volume for analyses and should accommodate sensors for monitoring various fluid parameters of the fluid. The apparatus should also permit control of fluid flow rate and pressure to suit specific separation and filtration requirements.

Existing separation and filtration equipment does not fulfil one or more of the above mentioned requirements. In particular, existing equipment does not facilitate sterilisation requiring disassembling of components and such equipment and often requiring substantial volumes of fluid for monitoring purposes. These drawbacks are particularly evident when dealing with the treatment of biological fluids, for example, blood in dialysis or life support systems. In addition, control of flow rate and pressure is often complex in existing equipment and further reduces the sterilisability of the equipment. Thus, most existing systems tend to be aseptic rather than sterile, and this is less desirable in a clinical environment.

It is an object of the present invention to provide fluid control apparatus which obviates or mitigates at least one of the aforementioned problems.

This is achieved by a fluid flow control apparatus in which a removable sterilisable or disposable element is provided and which includes pathways and connections between other sterilisable and/or disposable items.

According to a first aspect of the present invention there is provided fluid flow control apparatus for use with a fluid handling system, said apparatus comprising a fixed portion, and a sterilisable or disposable portion removably engageable with said fixed portion, said removable portion including a deformable fluid conduit, and said flow control apparatus includes flow restriction means for restricting flow in said deformable conduit, said flow restriction means being provided by an element which compresses said deformable conduit against a nip when said removable portion is engaged with said fixed portion to set the pressure in said fluid handling system, said removable portion being adapted to be coupled to pump means and to conduits in said fluid handling system and said fluid flow control apparatus having fluid pathways for permitting fluid to flow between inlet an output positions of said fluid flow control apparatus.

The said deformable conduit may be a separate flexible conduit adapted to be coupled between two ports on said removable portion or an integral moulded conduit disposed between two ports in said removable portion.

The fixed portion defines a recess for slidably receiving said removable portion. However, the removable portion can be engaged with said fixed portion by a clamp or other suitable fastener.

The fixed portion consists of two separate parts, a first guide part and a second flow restriction part, the first guide part defining the recess for slidably receiving the removable portion and the second flow restriction part being provided by the element engaging with a reaction element on said removable portion so that the deformable conduit is disposed therebetween when the fixed and removable parts are engaged.

The fluid flow control apparatus conveniently includes a fluid monitoring system, said fluid monitoring system comprising a conduit disposed in said removable portion which communicates with a main fluid conduit and said conduit having an outlet port, said first guide part having a first inlet port which sealably registers with said outlet port which said removable portion is engaged, said first inlet port being the inlet of a sampling, conduit, said sampling conduit communicating with at least one aperture for receiving a sensor for measuring a fluid parameter, said sampled fluid being passed to an outlet in said first guide part. A plurality of sensors are removably coupled to said first guide port for sensing various fluid parameters.

The fluid flow control apparatus may be used with a separation or filtration system such as a dialysis system for detoxifying blood or in a life support system.

The removable part and filter unit can be combined to form a single integral cassette which is disposable or sterilisable.

The fluid flow control may be used in a dialysis system, with the apparatus adapted to receive blood to be treated, said control apparatus having a sterilisable removable portion being coupled to pump means and to a separation or filtration element, said fluid flow restriction means being arranged to set a level of back pressure required for dialysis, blood monitoring means coupled to said sterilisable removable portion for receiving a sample of blood being passed to said separation element for analysing at least one parameter of said blood, and purge means coupled to said flow control apparatus for being coupled to a supply of purge fluid after said dialysis to purge said blood monitoring means of blood, and control means coupled to said control unit and to said pump means and said purge means for controlling the dialysis operation and setting the blood flow rate and separation pressure.

The fluid flow control apparatus can include pressure control means for controlling the transmembrane pressure in a filtration device, the pressure control means comprising filter means having an inlet for receiving an inlet fluid to be filtered and an outlet for receiving the concentrate from said filter means, first pressure monitoring means associated with an inlet conduit for measuring the inlet pressure to said filter means, second pressure monitoring means associated with the outlet conduit for measuring the pressure of the outlet fluid, means for comparing the inlet and outlet pressures measured and flow control means coupled to said first and second pressure monitoring means to provide a comparison signal, the flow control means being responsive to the comparison signal to control the flow of fluid through said filter unit to optimise control of the transmembrane pressure and filtration.

The fluid flow control means may be a pressure switch located in the inlet conduit or it can be located in the outlet conduit.

The pressure sensors can be disposed in a bleed line of the inlet and outlet conduits so that the fluid flows past the sensors or the pressure sensors can be diaphragm pressure sensors so that there is no contact between the fluid being treated and the pressure monitoring apparatus. The transmembrane pressure arrangement can be used in a plasma separation system having a first pump at said filter inlet, a second pump disposed at the filter outlet and a third pump disposed at the filtrate outlet, the filtrate outlet being adapted to be coupled to a reservoir of an anticoagulent substance and said filtrate output being connected to a plasma collection unit, the apparatus being arranged to separate plasma from blood donated by a patient, whereby in use, a first value of transmembrane pressure is used to actuate the first and third pumps to separate plasma and to store the separated plasma collection unit and a second value of transmembrane pressure is used to stop the first and third pumps and to actuate the second pump to return the blood to the patient.

These and other aspects of the present invention will become apparent from the following description when taken in combination with the accompanying drawings in which:-

Figure 1:
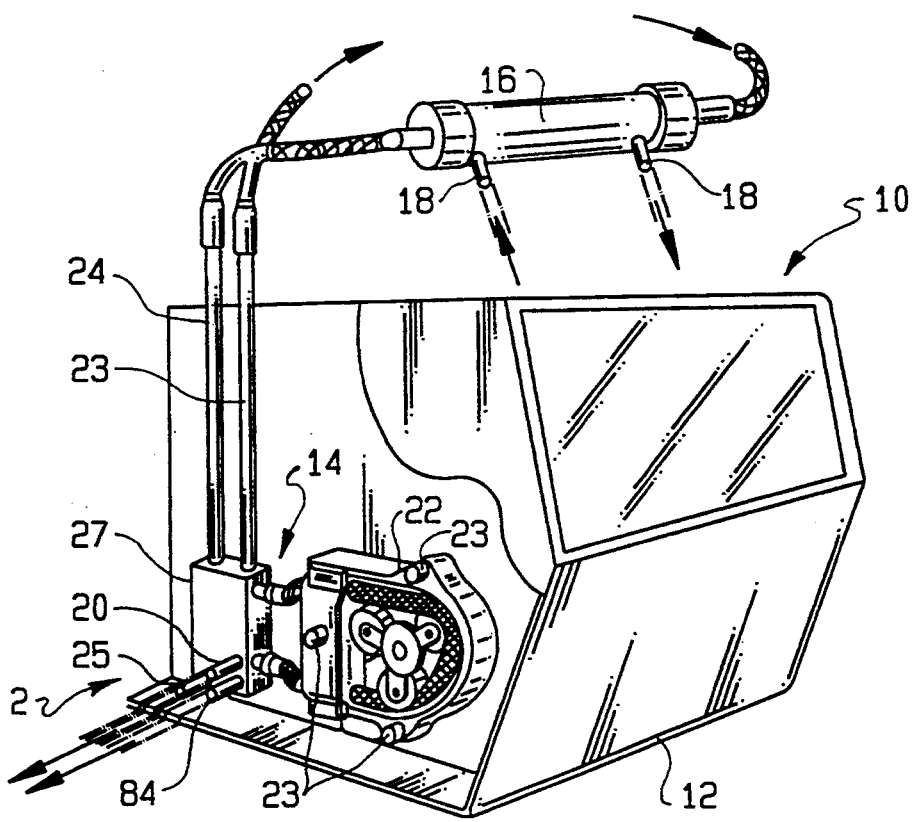
FIG. 1 is a perspective view of a fluid separation system incorporating fluid control apparatus in accordance with an embodiment of the the present invention.
Figure 2:
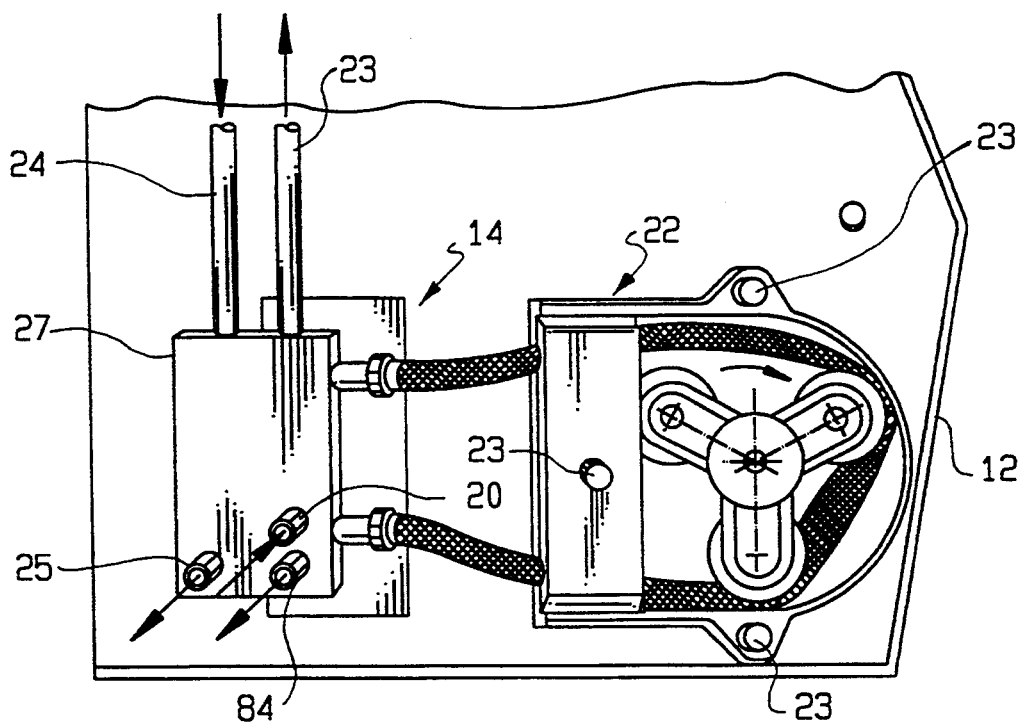
FIG. 2 is an elevational view of part of the apparatus shown in FIG. 1 taken in the direction of arrow 2 and drawn to a larger scale.

Reference is first made to FIGS. 1 and 2 of the drawings which shows a fluid separation system generally indicated by reference numeral 10. The fluid separation system 10 is depicted in use in a dialysis system where blood is taken from a patient and filtered through a semi-permeable membrane to remove waste products in the blood before the treated blood is returned to the patient. The system consists of a fluid control unit 12 incoporating fluid flow control apparatus 14 which receives blood from a patient and which passes the blood through a fluid handling system defined by a hollow fibre dialysis membrane 16 which is also connected via ports 18 to a dialysate reservoir (not shown) and the filtered or treated blood is returned to the patient via the fluid flow control apparatus as will be later described in detail.

Blood enters the apparatus 14 through main feed port 20 and is subsequently pumped through the apparatus by a 3-lobe peristaltic pump 22, along conduit 23 to the hollow fibre membrane 16. Filtered blood is returned via conduit 24 through fluid control apparatus 14 and is then returned to the patient via outlet tube 25. Parts of the fluid control unit 12, the tube in the peristaltic pump and filtration unit 16 are removable for sterilisation as will be described. The fluid control apparatus also comprises a sterilising purge system, a fluid monitoring arrangement and a transmembrane pressure monitoring system as will also be described.

The flow rate and pressure of blood in the system is controlled by pump 22 and flow control device 14. The operation of pump 22 is well known and forms no part of the invention. The pump cover can be removed using fasteners 23 to allow various parts to be replaced or sterilised if required.

Figure 3:
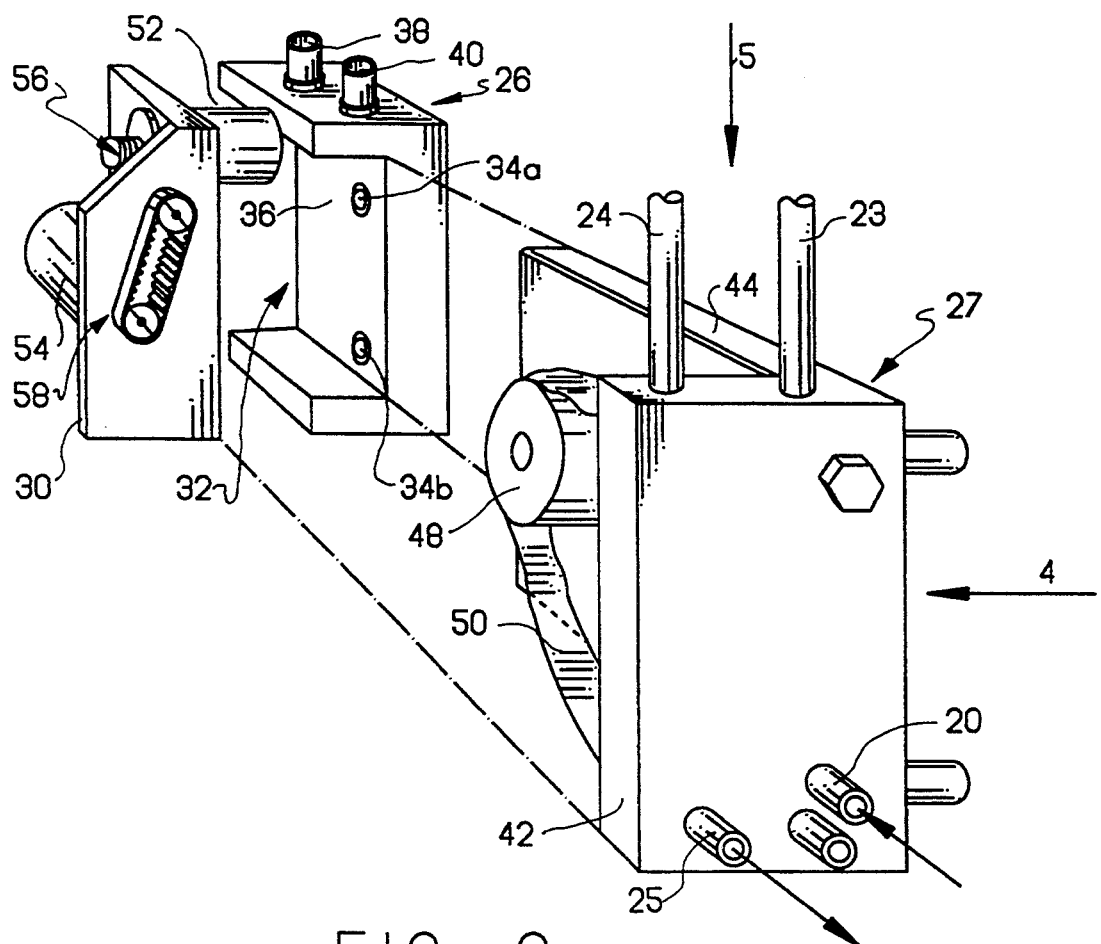
FIG. 3 is a perspective and partly exploded view of parts of the apparatus shown in FIG. 1.
Figure 4:
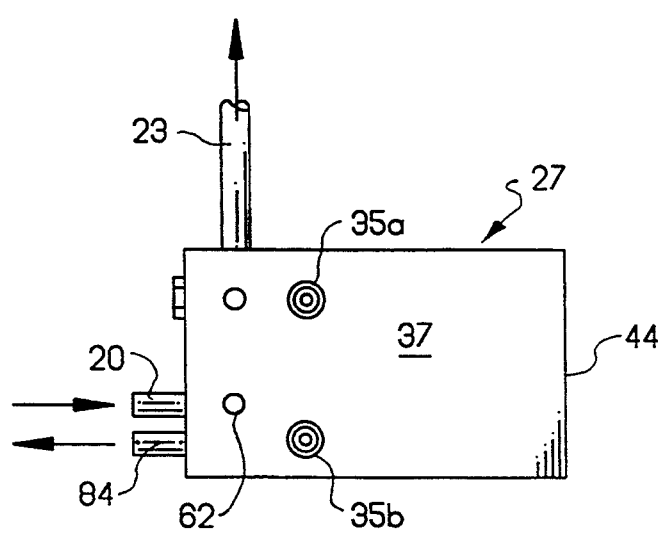
FIG. 4 is an elevational view of the apparatus of FIG. 3 taken in the direction of arrow 4 in FIG. 3.
Figure 5:
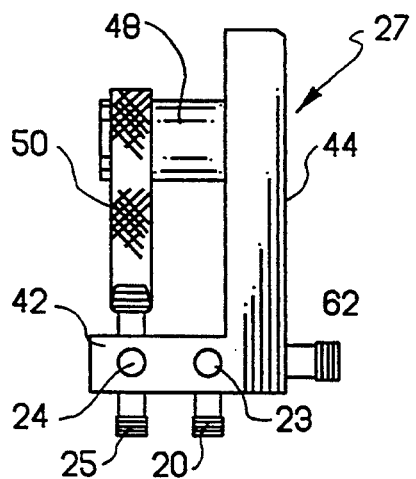
FIG. 5 is a plan view of the apparatus of FIG. 3 taken in the direction of arrow 5.

Reference is now made to FIGS. 3, 4 and 5 of the drawings which depict the fluid flow control apparatus 14 in greater detail. The fluid flow control apparatus 14 consists of two parts: a first main body portion, generally indicated by reference numeral 26, which remains fixed in the BIO 2000 control unit 12 and a removable cassette element 27. The main body portion 26 has two parts; a cassette guide 28 and a separate valve control part 30. The guide 28 and valve 30 are spaced apart to define a channel or recess 32 for slidably receiving the removable cassette element 27 in a close fitting arrangement.

The guide 28 has aseptic sampling ports 34a, b disposed on its inner surface 36 for registering with like ports 35a, b as disposed on the outer surface 37 of cassette element 27, as best seen in FIG. 4. In the assembled condition a pressure sensor 38 and pressure switch 40 are securely fastened in the top of the guide 28 to monitor this fluid pressure.

The cassette element 27 is generally L-shaped in plan and consists of machined blocks 42 and 44 of medical grade sterilisable stainless steel which are of sufficient thickness to accommodate fluid flow channels as will be fully explained later. The cassette element 27 contains the apparatus inlet 20 and various other inlets and outlets as will also be explained. The cassette also includes an element which is part of the control valve 30. This is a fixed cylindrical boss 48 around which is located a flexible conduit 50 which connects the conduit 24 tube with the unit outlet tube 25. The main part of control valve 30 includes a rotatable cam 52 coupled to an electric motor 54 via gears 56 and a chain and sprocket drive 58. When the cassette element 27 is in an assembled position as in FIG. 1 or 2, the electric motor is operable by a central control unit, (not shown) within apparatus 10, to control the position of cam 52 so that the distance between the cam 52 and boss 48 is controlled to define a 'nip' on tube 50 and thus compresses the tube. This nip and compression is used to create the back pressure in the separation element or filter 16 to suit the filtration requirements of the blood.

Figure 6:
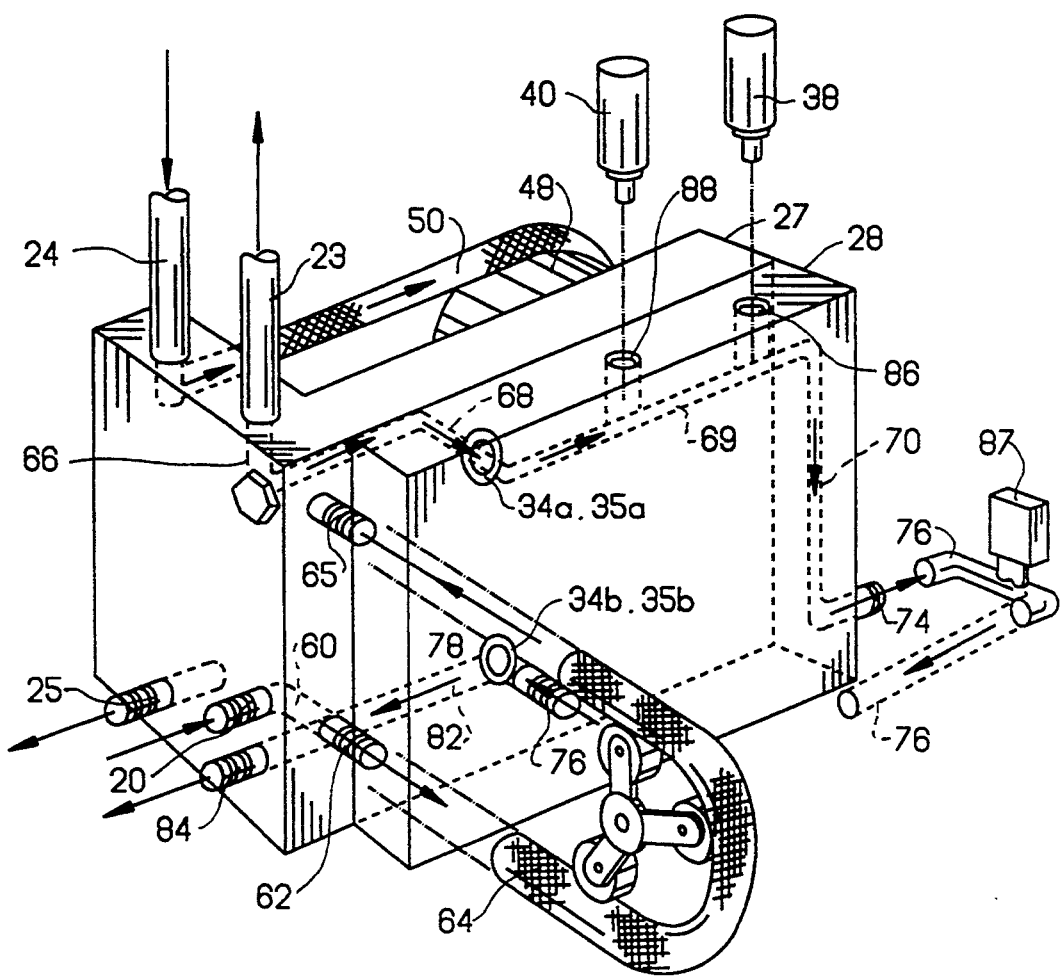
FIG. 6 is a partly assembled and perspective view of the fluid control apparatus shown in FIGS. 2 to 5, and FIG. 7. and 7a depicts an embodiment of fluid flow control apparatus in which the filter and cassette are combined in a single cassette.

Reference is now made to FIG. 6 of the drawings and for ease of understanding the blood flow path will be followed first. Blood to be treated is passed into the cassette element 27 via inlet 20 through internal conduit 60 (shown in broken outline) and via outlet 62 to conduit 64 of the 3-lobe peristaltic pump 22. The pumped blood is passed back to port 65 and, via internal conduit 66 the main volume of blood is passed through conduit 23 to the hollow fibre dialyser 16 for filtration a described below. A smaller volume of blood is passed along internal conduit 68 and aseptic ports 34a, 35a to internal conduit 69 disposed in the guide part 28. The internal conduit 69 travels downwardly in portion 70 and then exits guide part 28 via nozzle 74. To nozzle 74 is connected a conduit 76, the other end of which connects to a nozzle 78 disposed in the side of the guide part 28. The nozzle connects to the aseptic port 35b, 34b respectively to internal conduit 82 which leads to the outlet port 84.

There are drilled apertures, 86, 88 in the top of the guide part 28 which meet with internal conduit 69. The apertures receive sensors 38, 40 so that the leading ends of the sensors are disposed within the conduit 69 for monitoring blood parameters, in this case pH and temperature. A solenoid valve 87 is disposed in conduit 76 for controlling the start and finish of a purge operation as will be explained.

In operation, the system is connected up as shown in FIG. 1 and the system primed with blood in the usual manner. The control valve 30 is opened while the solenoid valve 87 is closed so that a volume of blood passes through the cassette 27. Pump 22 is then started to create flow and fluid is checked in the entire system. The pump speed is then set to provide the flow conditions appropriate for separation. The control valve 30 is then adjusted to set the back pressure appropriate to the membrane for filtration requirements. During operation pressure sensor 38, monitors the fluid pressure and control pressure switch 40.

In order to stop operation, the patient is disconnected and the main valve 30 and solenoid valve 87 are opened. A purging fluid is connected to between inlet port 20 and outlet port 84 and the residue of blood is flushed out of the dialysate system and the fluid flow; control system. The pump is then stopped but the system can continue to be purged or to drain. The cassette element 27 is readily removably by sliding into and out of engagement with the fixed guide 28 and the conduit 50 can be removed to allow the cassette element 27 to be sterilised. The aseptic ports 34a,b, 35a, b, ensure that the biological fluid is not contaminated and complies with existing safety requirements.

Various modifications can be made to the embodiment hereinbefore described without departing from the scope of the present invention. Any fluid having components which require to be filtered or separated can be used. Any other suitable form of membrane separator can be used, such as spirally wound or flat membranes as well as hollow fibre membranes. Other fluid parameters can be monitored using appropriate sensors instead of the pressure sensor and switch, for example viscosity and conductivity. The cassette can be made of sterilisable plastic instead of stainless steel and can also be disposable.

The conduit 50 need not be external but may be integral with a moulded plastic cassette but still being deformable in response to the cam to effect flow restriction. Although the fluid pathways in the removable cassette are internal it will be understood that the pathways could be external and in the form of tubes for example.

Figure 7:
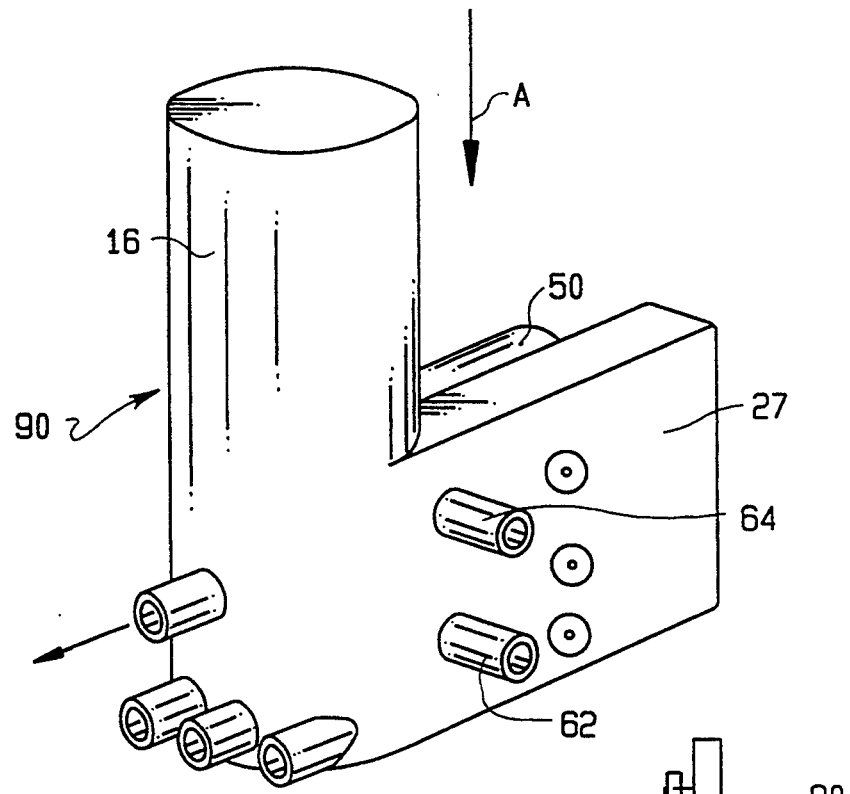
Figure 7A:
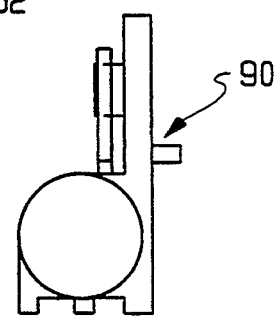

The cassette can be made as a unitary item; the filter 16 and lines can be combined with cassette 27 in an integral single unit 90 as best seen in the embodiment shown in FIGS. 7 and 7a. In this case the entire cassette assembly may be disposable or sterilisable.

In addition the flow restriction means could be disposed at any suitable location rather than in the flow control unit. For example the flow restriction means could be near or at the dialyser or the peristaltic pump. Control of the flow restriction means may be by a manual punch valve instead of the motor controlled operation. The cassette could be engaged with the fixed part other than by sliding, for example it could be placed in proximity to the fixed part and held thereat by a clamp. Furthermore the monitoring and purge system are not essential to every embodiment but only where an analysis of the fluid is required such as in the aforedescribed embodiment. Nevertheless, it is desirable to monitor certain parameters of most fluids being treated.

Figure 8:
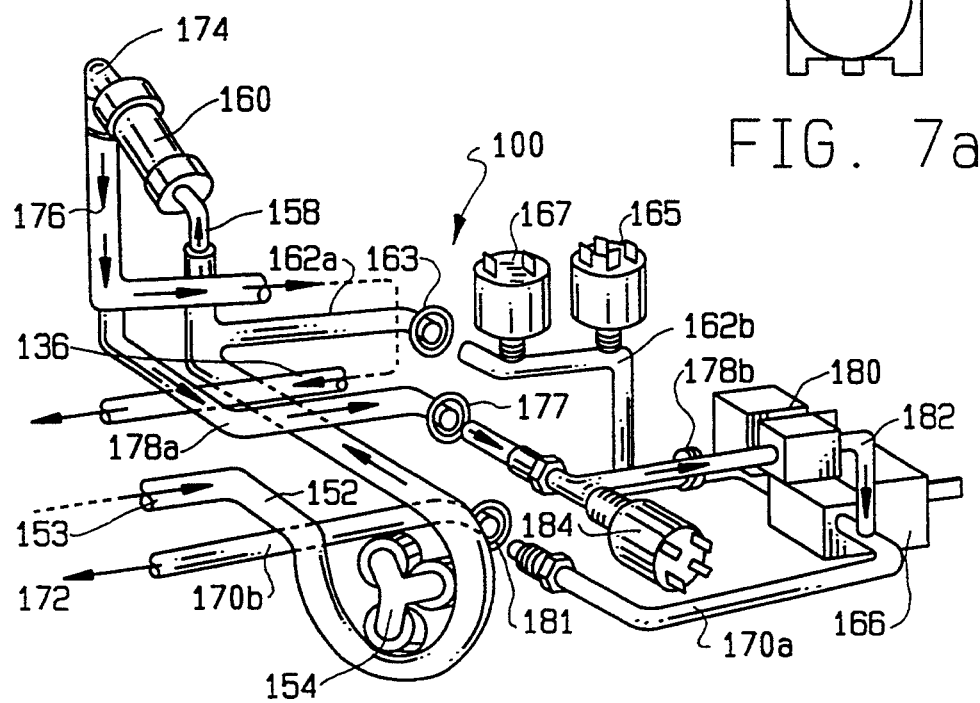
FIG. 8 is a diagrammatic representation of an embodiment of fluid flow control apparatus according to the present invention used in a transmembrane pressure monitoring application.

Reference is now made to FIG. 8 of the drawings which depicts a fluid circuit generally indicated by reference number 100 for use with a BIO 2000 filtration system (Bio-flow Ltd., U.K.), which can also be used with the embodiments of FIGS. 7, 7a. In the system shown in FIG. 8 a fluid conduit 152 has an inlet 153 for receiving fluid to be treated. A three lobe roller pump 154 forces the fluid along conduit 152 and through an inlet 158 to a hollow fibre filter unit generally shown by reference numeral 160. A bleed line 162a is taken from the inlet conduit 164 so that the inlet fluid can be monitored by various sensors. In the example shown, the pressure transducer 165 and pressure switch 167 are located in the bleed line 162a, for measuring the pressure parameters of the inlet fluid. The bleed line is fed to a solenoid valve 166, the output of which is connected to a conduit 170a which, in turn, is coupled via conduit 170b and outlet 172 to the system being treated.

The filter unit 160 has a filter output 174 which feeds outlet conduit 176 which passes through a pressure control valve, not shown in the interest of clarity, and the output from the valve constitutes the return fluid which is fed back to the source, in this example the vascular system of a patient. The outlet conduit 176 has a bleed line 178a which is connected to a second solenoid valve 180 which has an output 182 which feeds into conduit 170a as described above. A pressure transducer 184 is located in the bleed line 178a for measuring the pressure of the filter output fluid. It will be understood that conduits 162a, 178a and 170b are located in the removable portion 14 or cassette of the BIO 2000 filtration system when these conduits are coupled via aseptic ports 163, 177 and 181 to conduits 162b, 178b and 170a respectively which are located in the fixed portion 12.

In the arrangement shown in FIG. 8, the pressure switch 167 and pressure sensors 165 and 184 are located in line so that the fluid flows through and is in contact with the sensors.

With this arrangement, transmembrane pressure measurement (TMP) is achieved by monitoring the inlet pressure with transducer 165 and the outlet pressure with transducer 184. The transmembrane pressure is calculated as the average of the inlet and outlet pressures $(Po+Pi/2)$ less the filtrate pressure $(P_f)$. However, filtrate or permeate pressure is low and is generally taken as zero so that the average transmembrane pressure (TMP) is deemed to be the average of the inlet and outlet pressures. The measured pressures are processed in a routine manner to provide the average pressure used to control pressure switch 167 to vary the flow through the solenoid or to affect the back pressure of the system or the signal can be used to control the valve to vary the pressure in the filter outlet conduit by varying the distance between the cam and boss and thus affect the transmembrane pressure. With this arrangement, control of the transmembrane pressure is optimised to minimise effects of gel polarisation and the like which is a process which is known to slow down filtration.

A system generally similar to that shown in FIG. 8 can be used except that pressure is measured using diaphragm pressures sensors as opposed to a flow-through system which means that the fluid being filtered does not contact the monitoring sensor which maintains the sterility and the integrity of the fluid being treated.

Figure 9:
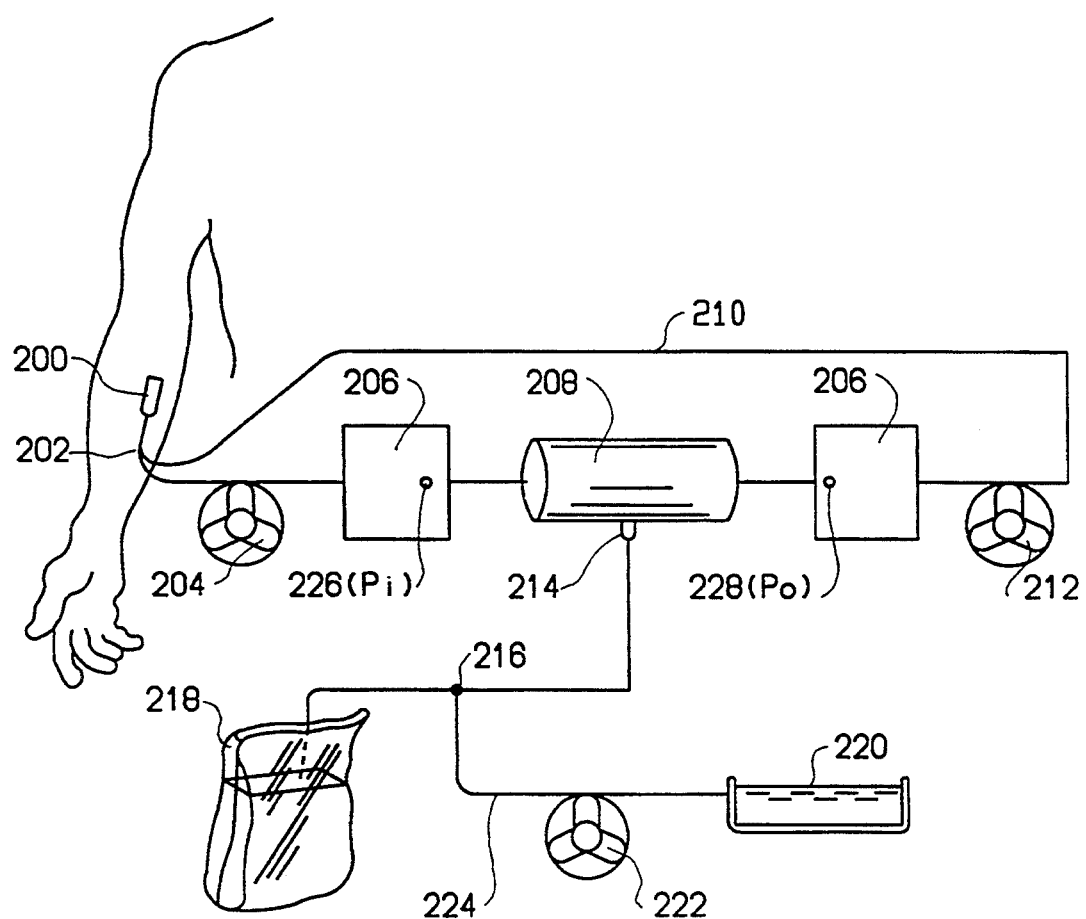
FIG. 9 is a diagrammatic representation of a further embodiment of fluid flow control apparatus according to the present invention using transmembrane pressure monitoring to control donor plasma separation.

An embodiment of the present invention set up for monitoring transmembrane pressure (TMP) will now be described in an application for controlling plasma donor separation and this is diagrammatically shown in FIG. 9

In this arrangement a vein of a patient is cannulated with a single needle shunt 200 and the blood is pumped through 2-way line 202 by a fast 3-lobe pump 204 through fluid flow control apparatus, general indicated by reference numeral 206 through hollow fibre filter 208 and back through the apparatus 206. The filter outlet line 210 is passed through a second 3-lobe pump 212 and is coupled via 2-way line 202 to the patient. The filtrate outlet 214 of the filter is coupled via fluid line 216 to a plasma collection bag 218 and anticoagulent is pumped from a reservoir 220 by a third 3-lobe pump 222 via line 224 into line 216 to prevent the plasma from coagulating.

The fluid control apparatus 206 has inlet and output pressure sensors 226, 228 which are used to monitor the transmembrane pressure (TMP) for controlling the plasma donor separation as will be described.

In operation the system is set up as shown and pump 204 is actuated to pump blood from the patient through the system. As the blood passes through the filter it is pumped by pump 222 to bag 218 while being combined with the anticoagulent. As the blood passes to the filter retentate outlet the inlet pressure ($P_i$) and outlet pressure ($P_o$) are monitored by sensors 226, 228 respectively and the transmembrane pressure (TMP) monitored.

When the TMP reaches a first preset value pumps 204, 222 are switched off and pump 212 switched on to return the cells in the fluid retentate back to the patient via lines 210 and 202. The TMP continues to be monitored and as the pressure falls, a second preset value is reached so that pumps 204, 222 are switched on and pump 212 is switched off to continue with further plasma separation. These procedures are repeated until sufficient plasma is separated.

It will be understood that the pressures in this application are monitored using the aforementioned pressure diaphragm sensors to avoid contact between the blood and the pressure monitoring circuitry which is an advantage of this arrangement. A further advantage is that no valves are required to control flow, this being achieved solely using the three pumps, which act as valves. Another advantage is that the total fluid line including the filter and bag is disposable. In this arrangement air bubble detectors are provided in the feed and return lines and, in the event of a bubble being detected, the whole system is shut down.

The apparatus hereinbefore described has application in other clinical areas such as life support systems as well as in the separation of substances from non-biological fluids, for example rare earth element or mineral separation. It will also be understood that the apparatus hereinbefore described can be used in different sizes, i.e. it can be scaled up to industrial plant size.

Advantages associated with the present invention are that the cassette is readily removeable to facilitate sterilisation and the fluid volume required for monitoring is very small, being less than 40 ml. The cassette can be disposable as can the entire filter and assembly in one embodiment. Also multi-point sensor access is provided to monitor various fluid parameters, and the sensors can be easily removed or replaced. In addition the pressure control for setting the filtration conditions is non-invasive and no contact is made with the fluid being treated which is important when using bioligical fluids. The transmembrane filtration/separation pressure can be readily and easily varied to suit specific filtration/separation applications and the equipment can be used with biological and non-biological fluids in various applications.

I claim:

1. Fluid flow control apparatus operable for use with a fluid handling system having a fluid handling inlet and a fluid handling outlet, said apparatus comprising:
   a. a fixed portion;
   b. a removable portion removably engageable with said fixed portion and removable for separate sterilizing or replacement, said removable portion including:
      1) a main inlet port for receiving fluid to be fed through said fluid handling system,
      2) a main outlet port for discharging fluid which has been fed through said fluid handling system,
      3) outlet conduit means located downstream of said main inlet port for connecting said control apparatus to said fluid handling inlet,
      4) inlet conduit means located upstream of said main outlet port for connecting said control apparatus to said fluid handling outlet, and
      5) a deformable fluid conduit connected between one of said main inlet and outlet ports and one of said outlet and inlet conduit means;
   c. fluid flow restriction means for restricting flow in said deformable conduit, said flow restriction means including a first element and a second element arranged for compressing said deformable conduit therebetween when said removable portion is engaged with said fixed portion, said flow restriction means being operable to selectively set a pressure in said deformable conduit and said fluid handling system;
   d. means for connecting a pump means between one of said main inlet and outlet ports and one of said outlet and inlet conduit means for pumping fluid through said control apparatus and said fluid handling system;
   e. fluid pathways, including said deformable fluid conduit, extending between said main inlet and outlet ports and said outlet and inlet conduit means for permitting fluid to flow between said inlet and said outlet ports when said removable portion is coupled to said fluid handling system and said pump means; and
   f. a fluid monitoring system, said fluid monitoring system comprising:
      1) a first sampling conduit disposed in said removable portion communicating with said main inlet port, said first sampling conduit having a first sampling outlet port,
      2) a first sampling inlet port in said fixed portion, said first sampling inlet port being arranged for sealably registering with said first sampling outlet port when said removable portion is engaged with said fixed portion, 3) a second sampling conduit, said second sampling conduit being located in said fixed portion, and having opposite ends, said first sampling inlet port defining an inlet at one end of said second sampling conduit, 4) at least one aperture in said fixed portion communicating with said second sampling conduit for receiving a sensor for measuring a fluid parameter, and 5) a second sampling outlet port in said fixed portion at the other end of said second sampling conduit.

2. Fluid flow control apparatus operable for use with a fluid handling system having a fluid handling inlet and a fluid handling outlet, said apparatus comprising:

a. a fixed portion;

b. a removable portion removably engageable with said fixed portion and removable for separate sterilizing or replacement, said removable portion including:

1) a main inlet port, 2) a main outlet port, 3) a first outlet conduit located downstream of said main inlet port for directing fluid flow to said fluid handling system, 4) a first inlet conduit located upstream of said main outlet port for receiving fluid flow from said fluid handling system, 5) a second outlet conduit operable for connecting said control apparatus to a pump inlet of a pump means for pumping fluid through said control apparatus and said fluid handling system, 6) a second inlet conduit operable for connecting said control apparatus to a pump outlet of said pump means leading to said fluid handling system, and 7) a deformable fluid conduit connected between one of said main inlet and outlet ports and one of said first outlet and inlet conduits;

c. fluid flow restriction means for restricting flow in said deformable conduit, said flow restriction means including a first element and a second element arranged for compressing said deformable conduit therebetween when said removable portion is engaged with said fixed portion, said flow restriction means being operable to selectively set a pressure in said deformable conduit and said fluid handling system;

d. fluid pathways, including said deformable fluid conduit, extending between said main inlet and outlet ports and said first and second outlet and inlet conduits for permitting fluid to flow between said inlet and said outlet ports; and e. a fluid monitoring system, said fluid monitoring system comprising:

1) a first sampling conduit disposed in said removable portion communicating with said main inlet port, said first sampling conduit having a first sampling outlet port, 2) a first sampling inlet port in said fixed portion, said first sampling inlet port being arranged for sealably registering with said first sampling outlet port when said removable portion is engaged with said fixed portion, 3) a second sampling conduit, said second sampling conduit being located in said fixed portion, and having opposite ends, said first sampling inlet port defining an inlet at one end of said second sampling conduit, 4) at least one aperture in said fixed portion communicating with said second sampling conduit for receiving a sensor for measuring a fluid parameter, and 5) a second sampling outlet port in said fixed portion at the other end of said second sampling conduit.

3. Fluid control apparatus as claimed in claim 2 wherein:

a. said deformable conduit is a flexible conduit.

4. Fluid control apparatus as claimed in claim 2 wherein:

a. said removable portion is constructed of moulded plastic; and b. said deformable conduit is an integral moulded part of said removable portion.

5. Fluid control apparatus as claimed in claim 2 wherein:

a. the fixed portion defines a recess for slideably receiving said removable portion.

6. Fluid control apparatus as claimed in claim 2 wherein:

a. the removable portion is constructed for engagement with said fixed portion by a fastener.

7. Fluid control apparatus as claimed in claim 2 wherein:

a. said fluid flow control apparatus is coupled to one of a separation and filtration system.

8. Fluid control apparatus as claimed in claim 7 wherein said fluid flow control apparatus is coupled to a life support system.

9. Fluid control apparatus as claimed in claim 2 wherein: each of a. said fluid flow control apparatus is coupled to a separation system; and b. the separation system is a dialysis system for detoxifying blood.

10. Fluid control apparatus as claimed in claim 2 wherein:

a. said removable portion is made of medical grade stainless steel.

11. Fluid control apparatus as claimed in claim 2 wherein:

a. said removable portion is made of sterilisable plastic.

12. Fluid control apparatus as claimed in claim 2 wherein:

a. the removable portion and the fluid handling system are combinable into a single integral structure which is removably coupled to the fixed portion.

13. Fluid flow control apparatus operable as claimed in claim 2 operable for use in a dialysis system for receiving blood to be treated, where said removable portion is coupled to said pump means and to a separation element and said fluid flow restriction means is arranged to set a level of back pressure required for dialysis, said apparatus further comprising:

a. monitoring means coupled to said removable portion for receiving a sample of blood being passed to said dialysis system for analyzing at least one parameter of said blood;

b. purge means coupled to the removable portion of said flow control apparatus for being coupled to a supply of purge fluid after said blood has been treated to purge said monitoring means of blood; and c. control means coupled to said fluid flow restriction means, to said pump means and to said purge means setting a blood flow rate and pressure of blood in said dialysis system.

14. Fluid flow control apparatus as claimed in claim 2 wherein said apparatus is coupled to a filtration device as the fluid handling system, said device including filter means connected between said first inlet and outlet conduits, said filter means having a filter inlet for receiving an inlet fluid to be filtered and a filter outlet for receiving concentrate from said filter means, said apparatus further comprising:
   a. first transmembrane pressure monitoring means associated with said filter inlet for measuring the transmembrane inlet pressure of said filter means;
   b. second transmembrane pressure monitoring means associated with said filter outlet for measuring the transmembrane outlet pressure of said filter means;
   c. means for comparing the inlet and outlet pressures measured; and
   d. flow control means coupled to said first and second pressure monitoring means for providing a comparison signal corresponding to the transmembrane pressures sensed by said first and second monitoring means, and in response to said signal, controlling the flow of fluid through said filter means to optimize control of the transmembrane pressures and filtration.

15. Fluid flow control apparatus as claimed in claim 14 wherein:
   a. the flow control means is a pressure switch located in communication with said filter inlet.

16. Fluid flow control apparatus as claimed in claim 14 wherein:
   a. the flow control means is a pressure switch located in communication with said filter outlet.

17. Fluid flow control apparatus as claimed in any one of claims 14 to 16 wherein:
   a. the pressure monitoring means are each disposed in a bleed line connected to said filter inlet and outlet so that the fluid flows past the respective monitoring means.

18. Fluid flow control apparatus as claimed in claim 17, further comprising:
   a. first and second solenoid valves coupled to the first and second pressure monitoring means, respectively, said valves having valve outputs which are combined into a single valve output conduit, said valves being actuatable to open said valve output conduit to permit purging of fluid from said bleed line.

19. Fluid flow control apparatus as claimed in any one of claims 14 to 16 wherein:
   a. the pressure monitoring means are each diaphragm pressure sensors so that there is no contact between the fluid being treated and the respective pressure monitoring means.

20. Fluid flow control apparatus as claimed in claim 14 wherein:
   a. said apparatus is coupled to a blood separation system including said filtration device and said filtration device includes a filtrate outlet for receiving filtrate from said filter means;
   b. said pump means includes
      1) a first pump disposed at said filter inlet,
      2) a second pump disposed at said filter outlet,
      3) a third pump disposed at the filtrate outlet, the filtrate outlet being adapted to be connected to a reservoir of an anticoagulant substance and said filtrate outlet being further adapted to be connected to a plasma collection unit; and
   the device being effective to separate plasma from blood donated by a patient, whereby in use, a first value of transmembrane pressure is used to actuate the first and third pumps to separate plasma and to store the separated plasma in a collection unit and a second value of transmembrane pressure is used to stop the first and third pumps and to actuate the second pump to return the blood to the patient.

21. Fluid control apparatus operable for use with a fluid handling system having a fluid handling inlet and a fluid handling outlet, said apparatus comprising:
   a. a fixed portion;
   b. a removable portion removably and slidably engageable with said fixed portion and removable for separate sterilizing or replacement, said removable portion including:
      1) a main inlet port,
      2) a main outlet port,
      3) a first outlet conduit for directing fluid flow to said fluid handling system,
      4) a first inlet conduit for receiving fluid flow from said fluid handling system,
      5) a second outlet conduit for connecting said control apparatus to a pump inlet of a pump means for pumping fluid through said control apparatus and said fluid handling system,
      6) a second inlet conduit for connecting said control apparatus to a pump outlet of said pump means, said pump outlet leading to said control apparatus and said fluid handling system, and
      7) a deformable fluid conduit connected between one of said main inlet and outlet ports and one of said first outlet and inlet conduits;
   c. fluid flow restriction means for restricting flow in said deformable conduit, said flow restriction means including a first element and a second element arranged for compressing said deformable conduit therebetween when said removable portion is engaged with said fixed portion, said flow restriction means being operable to set a pressure in said deformable conduit and said fluid handling system; and
   d. fluid pathways, including said deformable fluid conduit, extending between said main inlet and outlet ports and said first and second outlet and inlet conduits for permitting fluid to flow between said inlet and said outlet ports;
   wherein the fixed portion consists of two separate parts including:
      1) a first guide part defining a recess for slideably receiving the removable portion, and
      2) a second flow restriction valve control part being defined by said first element disposed in opposing relation to said second element with the deformable conduit disposed therebetween when the fixed and removable portions are engaged and
   said second element is mounted on said removable portion.

22. Fluid control apparatus as claimed in claim 21 further comprising:
   a fluid monitoring system said fluid monitoring system comprising:
      1) a first sampling conduit disposed in said removable portion communicating with said main inlet port, said first sampling conduit having a first sampling outlet port, 2) a first sampling inlet port in said first guide part, said first sampling inlet port being arranged for sealably registering with said first sampling outlet port when said removable portion is engaged with said fixed portion, 3) a second sampling conduit, said second sampling conduit being located in said first guide part, and having opposite ends, said first sampling inlet port defining an inlet at one end of said second sampling conduit, 4) at least one aperture in said first guide part communicating with said second sampling conduit and operable for receiving a sensor for measuring a fluid parameter, and 5) a second sampling outlet port in said first guide part at the other end of said second sampling conduit.

23. Fluid control apparatus as claimed in claim 22 wherein:

said at least one apertures comprises a plurality of apertures and provided; and one of said sensors is removably coupled to each of said apertures in said first guide part is removably couplable to a sensor for sensing one of various fluid parameters.

24. Fluid control apparatus as claimed in claim 22, further comprising:

a. an openable and closable outlet purge port;

b. purge conduit means connecting said second sampling outlet port to said outlet purge port; and c. purge valve means communicating with said outlet purge port for selectively opening and closing said outlet purge port to permit purging of fluid in said second sampling conduit through said outlet purge port when said outlet purge port is open.

25. Fluid control apparatus as claimed in claim 24 further comprising:

a. a second sampling inlet port in said removable portion for sealingly registering with said second sampling outlet port when said removable portion is engaged with said fixed portion;

b. said purge conduit means includes a purge conduit in said removable portion connected between said outlet purge port and said second sampling inlet port; and c. said second sampling outlet port is disposed downstream of said purge valve means relative to the direction of said purging.

26. Fluid control apparatus as claimed in claim 22 or 25, wherein:

a. said sampling ports are aseptic ports.

27. Fluid flow control apparatus operable for use with a fluid handling system having a fluid handling inlet and a fluid handling outlet, said apparatus comprising:

a. a fixed portion;

b. a removable and separable portion removably engageable with said fixed portion and removable to a location spaced from said fixed portion for separate sterilizing or replacement, said removable portion including:

1) a main inlet port for receiving fluid to be fed through said fluid handling system, 2) a main outlet port for discharging fluid which has been fed through said fluid handling system, 3) outlet conduit means located downstream of said main inlet port for connecting said control apparatus to said fluid handling inlet, 4) inlet conduit means located upstream of said main outlet port for connecting said control apparatus to said fluid handling outlet, and 5) a deformable fluid conduit connected between one of said main inlet and outlet ports and one of said outlet and inlet conduit means;

c. fluid flow restriction means for restricting flow in said deformable conduit, said flow restriction means including a first element comprising an adjustable cam means mounted on said fixed portion and a second element comprising a roller mounted on said removable portion and about which said deformable conduit is arranged, said elements being arranged for compressing said deformable conduit therebetween when said removable portion is engaged with said fixed portion, said flow restriction means being operable to selectively set a pressure in said deformable conduit and said fluid handling system;

d. means for connecting a pump means between one of said main inlet and outlet ports and one of said outlet and inlet conduit means for pumping fluid through said control apparatus and said fluid handling system; and e. fluid pathways, including said deformable fluid conduit, extending between said main inlet and outlet ports and said outlet and inlet conduit means for permitting fluid to flow between said inlet and said outlet ports when said removable portion is coupled to said fluid handling system and said pump means.

* * * * *